(12) United States Patent  
Clifton

(10) Patent No.: US 9,390,499 B2
(45) Date of Patent: Jul. 12, 2016

(54) METHODS AND APPARATUS FOR IMAGE PROCESSING, AND LASER SCANNING OPHTHALMOSCOPE HAVING AN IMAGE PROCESSING APPARATUS

(71) Applicant: Optos PLC, Dunfermline (GB)

(72) Inventor: David Clifton, Shandon (GB)

(73) Assignee: Optos PLC, Dunfermline (GB)

(*) Notice: Subject to any disclaimer, the term of this patent is extended or adjusted under 35 U.S.C. 154(b) by 0 days.

(21) Appl. No.: 14/404,162

(22) PCT Filed: May 28, 2013

(86) PCT No.: PCT/GB2013/051412
§ 371 (c)(1),
(2) Date: Nov. 26, 2014

(87) PCT Pub. No.: WO2013/179021
PCT Pub. Date: Dec. 5, 2013

(65) Prior Publication Data
US 2015/0254849 A1    Sep. 10, 2015

(30) Foreign Application Priority Data

May 28, 2012 (GB) .................................. 1209390.2

(51) Int. Cl.
*G06K 9/00* (2006.01)
*G06T 7/00* (2006.01)
(Continued)

(52) U.S. Cl.
CPC ............. *G06T 7/0014* (2013.01); *A61B 3/1225* (2013.01); *G06K 9/0061* (2013.01); *G06K 9/4628* (2013.01); *G06T 3/0068* (2013.01); *G06T 3/0093* (2013.01); *G06T 7/0016* (2013.01); *G06T 7/402* (2013.01);
(Continued)

(58) Field of Classification Search
CPC .............. G06K 9/00; G06T 7/00; A61B 3/00
USPC ........... 382/128–134, 196, 270; 600/108, 310
See application file for complete search history.

(56) References Cited

U.S. PATENT DOCUMENTS

| | | | |
|---|---|---|---|
| 8,478,376 B2* | 7/2013 | Van Slyke | A61B 5/14551 600/310 |
| 8,781,197 B2* | 7/2014 | Wang | G01R 33/54 382/131 |
| 2010/0014761 A1 | 1/2010 | Addison et al. | |

FOREIGN PATENT DOCUMENTS

EP        0730428 A1    9/1996
WO   WO-2008009877 A1  1/2008

OTHER PUBLICATIONS

Salvador, Elena, "International Search Report," prepared for PCT/GB2013/051412, as mailed Sep. 2, 2013, three pages.
(Continued)

*Primary Examiner* — Abolfazl Tabatabai
(74) *Attorney, Agent, or Firm* — Winstead PC

(57) ABSTRACT

A laser scanning ophthalmoscope obtains images of a retina. An image is processed by (i) mapping an image along a one dimensional slice; (ii) computing a wavelet scalogram of the slice; (iii) mapping ridge features from the wavelet scalogram; repeating steps (i), (ii) and (iii) for one or more mapped image slices. The mapped ridge features from the slices are superimposed. Textural information is derived from the superimposed mapped ridge features. The analysis can be tuned to detect various textural features, for example to detect image artifacts, or for retinal pathology classification.

19 Claims, 16 Drawing Sheets

(51) Int. Cl.
*G06T 7/40* (2006.01)
*A61B 3/12* (2006.01)
*G06K 9/46* (2006.01)
*G06T 3/00* (2006.01)
*A61B 1/04* (2006.01)
*A61B 5/00* (2006.01)

(52) U.S. Cl.
CPC ............... *G06K2009/00932* (2013.01); *G06T 2207/10004* (2013.01); *G06T 2207/10024* (2013.01); *G06T 2207/10056* (2013.01); *G06T 2207/20016* (2013.01); *G06T 2207/20032* (2013.01); *G06T 2207/20036* (2013.01); *G06T 2207/20064* (2013.01); *G06T 2207/30041* (2013.01); *G06T 2207/30201* (2013.01)

(56) References Cited

OTHER PUBLICATIONS

Prakash, Surya, et al., "Segmenting Multiple Textured Objects Using Geodesic Active Contour and DWT," Dec. 18, 2007, pp. 111-118.
Xiong, Yingen, et al., "Hand Motion Gesture Frequency Properties and Multimodal Discourse Analysis," International Journal of Computer Vision, vol. 69, No. 3, Apr. 1, 2006, pp. 353-371.

\* cited by examiner

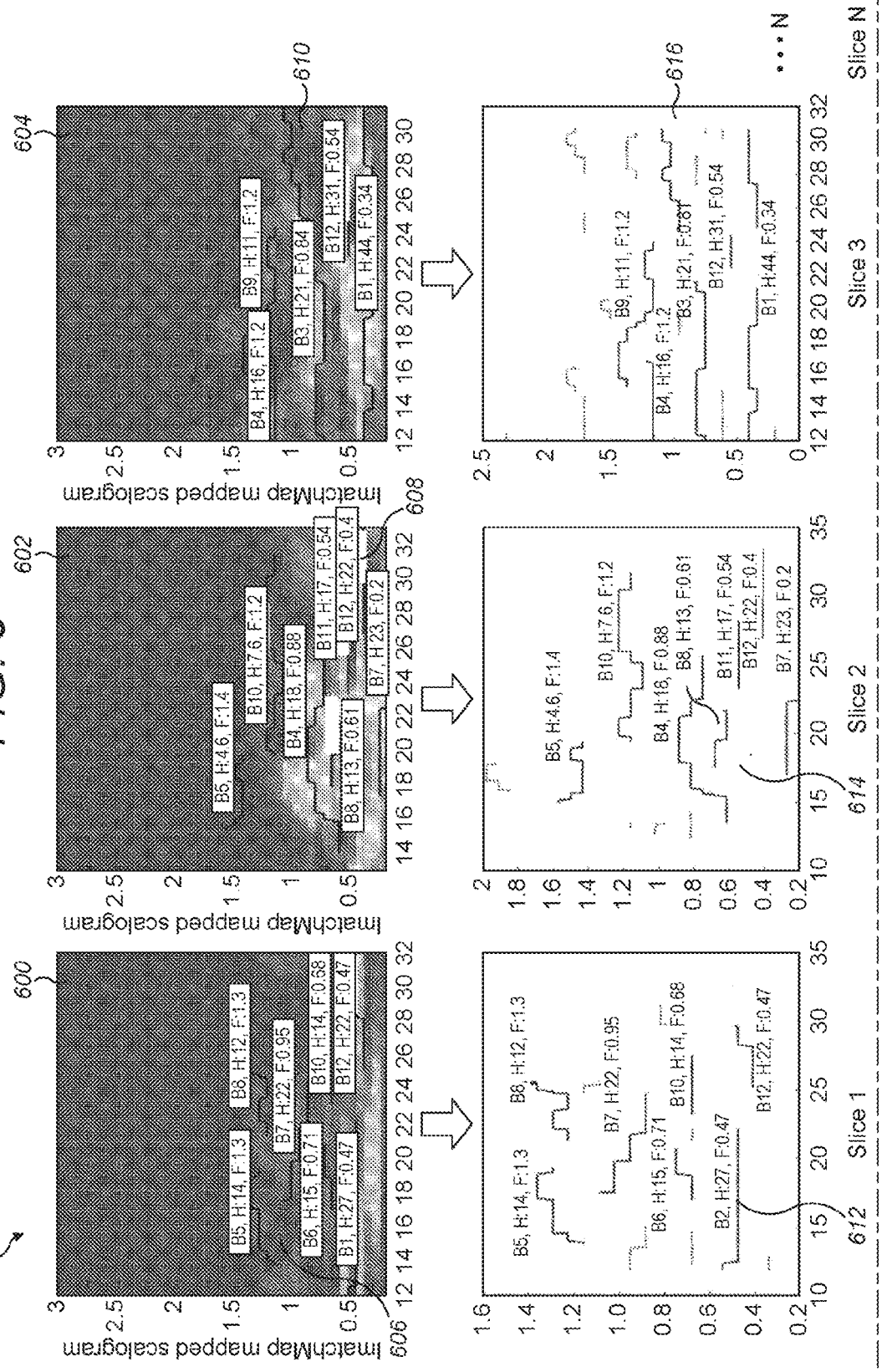

Selected image segment

METHODS AND APPARATUS FOR IMAGE PROCESSING, AND LASER SCANNING OPHTHALMOSCOPE HAVING AN IMAGE PROCESSING APPARATUS

FIELD

The present invention relates to image processing, more particularly to methods and apparatus for image processing, and laser scanning ophthalmoscope having an image processing apparatus. In one example, the present invention relates to but not exclusively to methods of textural analysis applied in the field of ocular imaging.

BACKGROUND

It is well known to capture image data using digital image sensors. An array of light sensitive picture elements (pixels) is provided, which can be manufactured as charge coupled devices or using complementary metal oxide semiconductor (CMOS) techniques. Incident radiation causes a charge to be generated at each pixel. This charge is converted to a voltage whose value is then digitised. The value of the voltage depends upon the intensity of the illumination incident on the pixel during an integration time, when the pixels are set in a light sensitive mode. A pixel array can be formed in one, two or three dimensions. The most common form is a two dimensional pixel array as found in everyday cameras for example. A one dimensional pixel array is typically referred to as a "linear array", and an image sensor with such an array can be termed a linear sensor or a linear scanner.

The set of intensity values derived from the pixel array is known as image data. The "raw" image data output by the pixel array may be subjected to various post-processing techniques in order to reproduce an image either for viewing by a person or for processing by a machine. These post-processing techniques can include various statistical methods for image analysis and for performing various camera and image processing functions.

One example of such techniques is the recognition and/or classification of textures within an image. The texture can represent surface characteristics of an object or region, and can be used as a basis for identifying different objects or different regions of an object within an image. Modelling texture is usually characterised by variations in signal intensity, and sometimes the spatial relationship (local neighbourhood properties) of these variations in an image.

It is know to use two dimensional wavelet transforms in a method for modelling texture. Wavelet transforms are useful because they give the ability to construct a time-frequency representation of a signal that offers very good time and frequency localisation.

An introduction to wavelets can be found from US 2010/0014761 and is provided below in the detailed description section.

However these methods are not tolerant to fragmentation of the textural features being measured, that is, when the textural features comprise diffuse, irregular, broken or spaced patterns in the image. There are also limits to the resolution and resolving power of existing techniques.

There is therefore a need for a method that is more robust to fragmentation in the textural images, and/or that has improved resolution, and/or that has an improved resolving power with respect to existing wavelet based techniques.

SUMMARY

According to a first aspect of the invention there is provided a method of image processing comprising:

(i) mapping an image along a one dimensional slice;
(ii) computing a wavelet scalogram of the slice;
(iii) mapping ridge features within the wavelet scalogram;
repeating steps (i), (ii) and (iii) for one or more mapped image slices;
superimposing the mapped ridge features from the slices; and deriving textural information from said superimposed mapped ridge features.

Because the textural analysis is performed based on the extracted ridge features only, the method provides robust, reliable performance in cases where the textural features being measured are fragmented.

Optionally, said step of deriving textural information from said superimposed mapped ridge features comprises thresholding or deriving statistics from a histogram representation of the 2D frequency and scale space spanning the mapped ridge features.

Optionally, said step of mapping an image along a one dimensional slice comprises selecting a row or column of image data from the image;

Alternatively, said step of mapping an image along a one dimensional slice comprises mapping a path along a set of image data pixels to a straight line representation.

Optionally, said path along a set of image data pixels comprises a straight line which is angled away from the horizontal or vertical axes defined by the rows and columns of the image data pixels.

Optionally, said path along a set of image data pixels comprises a circular path, or part thereof.

Optionally, said selected row or column or said path is chosen to have a directionality which corresponds to a directionality of a characteristic of the image which is expected or is being searched for.

Optionally, said characteristic of the image is a feature associated with a known pathology or medical condition.

Examples of these pathologies or conditions include retinal ischemic areas, macular degeneration, or other regions of retinal pathologies.

Optionally, said derived textural information is used to classify regions of a retinal image as comprising either retinal texture, or texture which comprises lid or lashes.

Optionally, the regions comprising lid or lash textures are excluded from a subsequent further image analysis and/or examination procedure.

Optionally, said derived textural information is used to identify scanner-specific image anomalies.

Examples include subtle, periodic variations in image intensity that occur due to inaccuracies in optical scan components.

Optionally, the step of computing a wavelet scalogram of the slice comprises application of a continuous wavelet transform.

Optionally, the step of computing a wavelet scalogram comprises selecting a characteristic frequency of the applied wavelet transform to match a chosen shape.

Optionally, the step of computing a wavelet scalogram comprises selecting a scale of the applied wavelet transform to match a chosen feature size.

The selection of one of both of a characteristic frequency and a scale of the applied wavelet transform allows it to be tuned to latch on to features of interest, which are expected to be present in an image or which are being searched for.

Optionally, a characteristic frequency and a scale are chosen to match the size and shape of rods and/or cones in a retina.

According to a second aspect of the present invention there is provided an image processing apparatus comprising:

means for receiving image data from an image sensor; and a processor arranged to:
(i) map an image along a one dimensional slice;
(ii) compute a wavelet scalogram of the slice;
(iii) map ridge features within the wavelet scalogram;
repeat steps (i), (ii) and (iii) for one or more mapped image slices;
superimpose the mapped ridge features from the slices; and
derive textural information from said superimposed mapped ridge features.

Optionally, the apparatus is arranged to perform the methods of the features defined above.

According to a third aspect of the present invention there is provided a laser scanning ophthalmoscope having an image processing apparatus comprising:
means for receiving image data from an image sensor; and a processor arranged to:
(i) map an image along a one dimensional slice;
(ii) compute a wavelet scalogram of the slice;
(iii) map ridge features within the wavelet scalogram;
repeat steps (i), (ii) and (iii) for one or more mapped image slices;
superimpose the mapped ridge features from the slices; and
derive textural information from said superimposed mapped ridge features.

According to a fourth aspect of the present invention there is provided a computer program product encoded with instructions that when run on a computer, cause the computer to receive image data and perform a method of image processing comprising:
(i) mapping an image along a one dimensional slice;
(ii) computing a wavelet scalogram of the slice;
(iii) mapping ridge features within the wavelet scalogram;
repeating steps (i), (ii) and (iii) for one or more mapped image slices;
superimposing the mapped ridge features from the slices; and
deriving textural information from said superimposed mapped ridge features.

The computer program product may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

BRIEF DESCRIPTION OF THE DRAWINGS

Embodiments of the present invention are described, by way of example only, with reference to the accompanying drawings in which.

DETAILED DESCRIPTION

Figure 1:
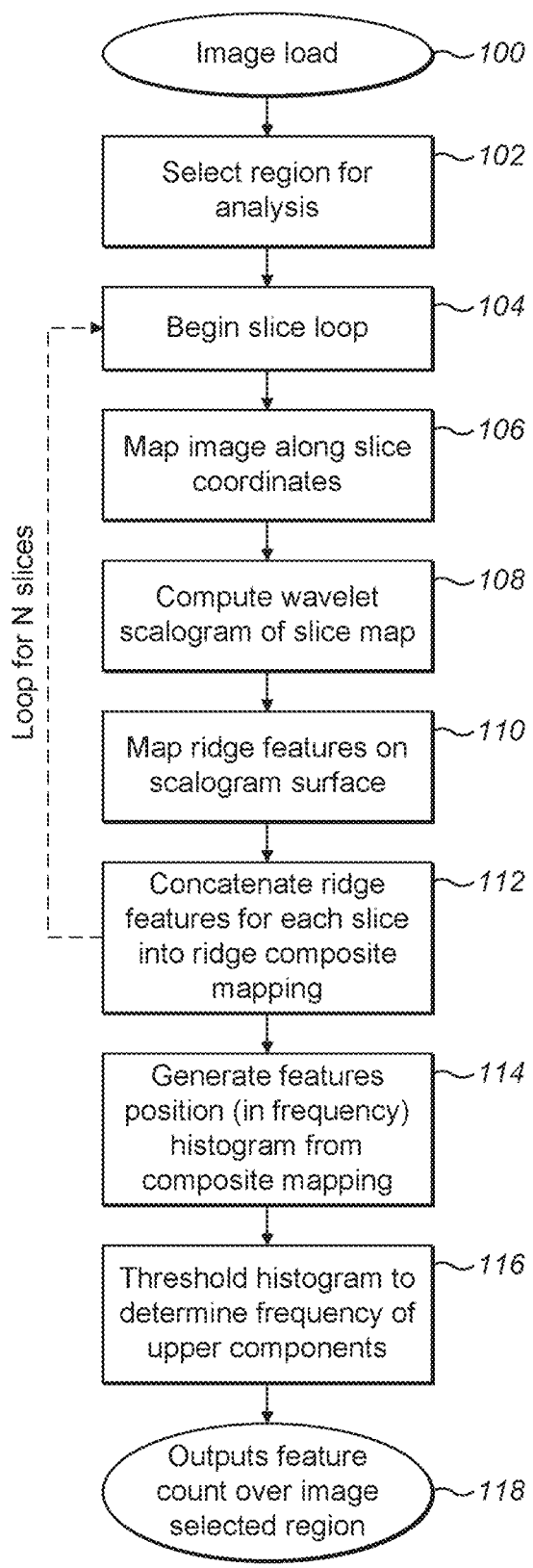
FIG. 1 illustrates steps of an exemplary algorithm according to a first embodiment of the present invention.

The following introductory description of wavelets is taken from US 2010/0014761, with some minor modifications:

Introduction to Wavelet Transform

The continuous wavelet transform of a signal x(t) in accordance with the present disclosure may be defined as $$T(a, b) = \frac{1}{\sqrt{a}} \int_{-\infty}^{+\infty} x(t) \psi * \left(\frac{t-b}{a}\right) dt \quad \text{(equation 1)}$$

where ψ*(t) is the complex conjugate of the wavelet function ψ(t), a is the dilation parameter of the wavelet and b is the location parameter of the wavelet. The transform given by equation (1) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

The energy density function of the wavelet transform, the scalogram, is defined as $$S(a,b) = |T(a,b)|^2 \quad \text{(equation 2)}$$

where '||' is the modulus operator. The scalogram may be rescaled for useful purposes. One common resealing is defined as $$S_R(a, b) = \frac{|T(a, b)|^2}{a} \quad \text{(equation 3)}$$

and is useful for defining ridges in wavelet space when, for example, the Morlet wavelet is used. Ridges are defined as the locus of points of local maxima in the plane.

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear rescaling, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by:

$$f = \frac{fc}{a} \quad \text{(equation 4)}$$

where fc, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{(i2\pi f_0)^2/2})e^{-t^2/2} \quad \text{(equation 5)}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 >> 0$ and can be ignored, in which case, the Morlet wavelet can be written in a simpler form as $$\psi(t) = \frac{1}{\pi^{1/4}} e^{i2\pi f_0 t} e^{-t^2/2} \quad \text{(equation 6)}$$

This wavelet is a complex wave within a scaled Gaussian envelope. While both definitions of the Morlet wavelet are included herein, the function of equation (6) is not strictly a wavelet as it has a non-zero mean (i.e., the zero frequency term of its corresponding energy spectrum is non-zero). However, it will be recognized by those skilled in the art that equation (6) may be used in practice with f0>>0 with minimal error and is included (as well as other similar near wavelet functions) in the definition of a wavelet herein.

An Introduction to Image Forming

As described above, the present disclosure provides for the use of a wavelet transform for the parameterisation of the rate of occurrence, or density, of a certain feature (or features of similar characteristics) in an image. In one embodiment, an overview of an algorithm for performing an exemplary method of the disclosure is shown in FIG. 1. Where the conventional use of wavelet analysis refers to time-varying waveforms and temporal frequencies, the skilled reader will understand that the same technique can be adapted to process images having spatial frequency characteristics.

The method illustrated in FIG. 1 comprises the steps of loading an image 100, selecting a region for analysis 102, beginning a slice loop 104, mapping the image along slice coordinates 106, computing a wavelet scalogram of a slice map 108, mapping ridge features on the scalogram surface 110, and superimposing ridge features for each slice into a ridge composite mapping 112. Steps 104-112 are then looped N times, for N slices, following the end of the slice loop, i.e. when a counter has reached N. The method then proceeds with a step of generating a featured position (in spatial frequency) histogram from the composite mapping 114, thresholding the histogram to determine frequency of upper components 116 and outputting a feature count over the image selected region 118. It is understood by the skilled person that it is not necessary to arrange the superimposing step within the slice loop. For example, at the end of the slice loop, the ridge features are mapped on the scalogram surface of each image slice. With the mapped ridge features from each image slice, the superimposing step can be performed after each slice within the slice loop or in a separate loop to obtain a ridge composite mapping.

FIGS. 2-6 illustrate various aspects of these steps, applied for the specific example of computing a density estimation for retinal rod and cone features. This is achieved by tuning the wavelet characteristics to latch to the required features characteristic of rods and cones.

The tuning of a wavelet is achieved through the adjustment of its characteristic frequency, $f_c$ (which defines the shape that can be latched), and a selection of the scale, a (which defines, in effect, the feature size that can be latched). These parameters are explained above with reference to equation (4). Particular values of $f_c$ and a can be chosen based on known typical size and shape of rods and cones in a typical eye. It is to be appreciated that in general the wavelet can be selected to be tuned for other textural features such as for example, image artefacts arising from the physical structure of the image scanning arrays or a lid/lash classification or retinal pathology classification.

Figure 2:
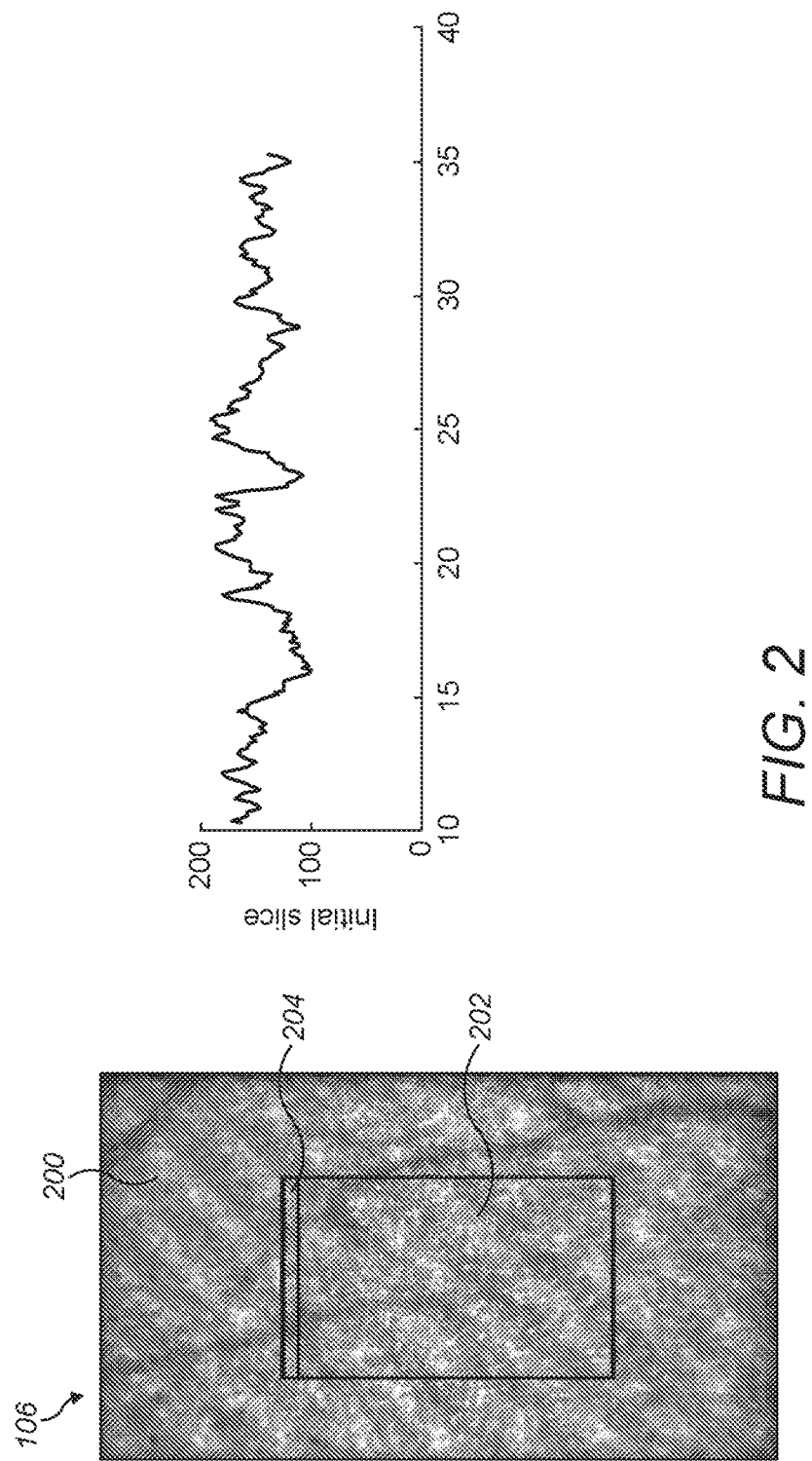
FIG. 2 illustrates aspects of the step of mapping an image along slice coordinates illustrated in FIG. 1.

FIG. 2 illustrates aspects of step 106; that of mapping an image along slice coordinates. An image 200 is shown from which a region 202 is selected for analysis. Here the region 202 is represented by a two dimensional pixel array. In one embodiment, each of the slices may comprise successive horizontal rows of the selected region 202. FIG. 2 also shows a graph plotting the signal intensity on the y axis versus the horizontal position along the slice, on the x axis.

The mapping of the slices can be at any orientation so long as the slices are parallel to each other. Sliced positions are incremented by a pixel spacing of at least half the pixel width of the cone/rod features. This minimum spacing corresponds to the Nyquist frequency of the patterns of interest.

During or following on from the looping of the slices (repetition of steps 104 through 112 of FIG. 1), the data from successive slices can be superimposed and can be plotted on the same graph.

Figure 3:
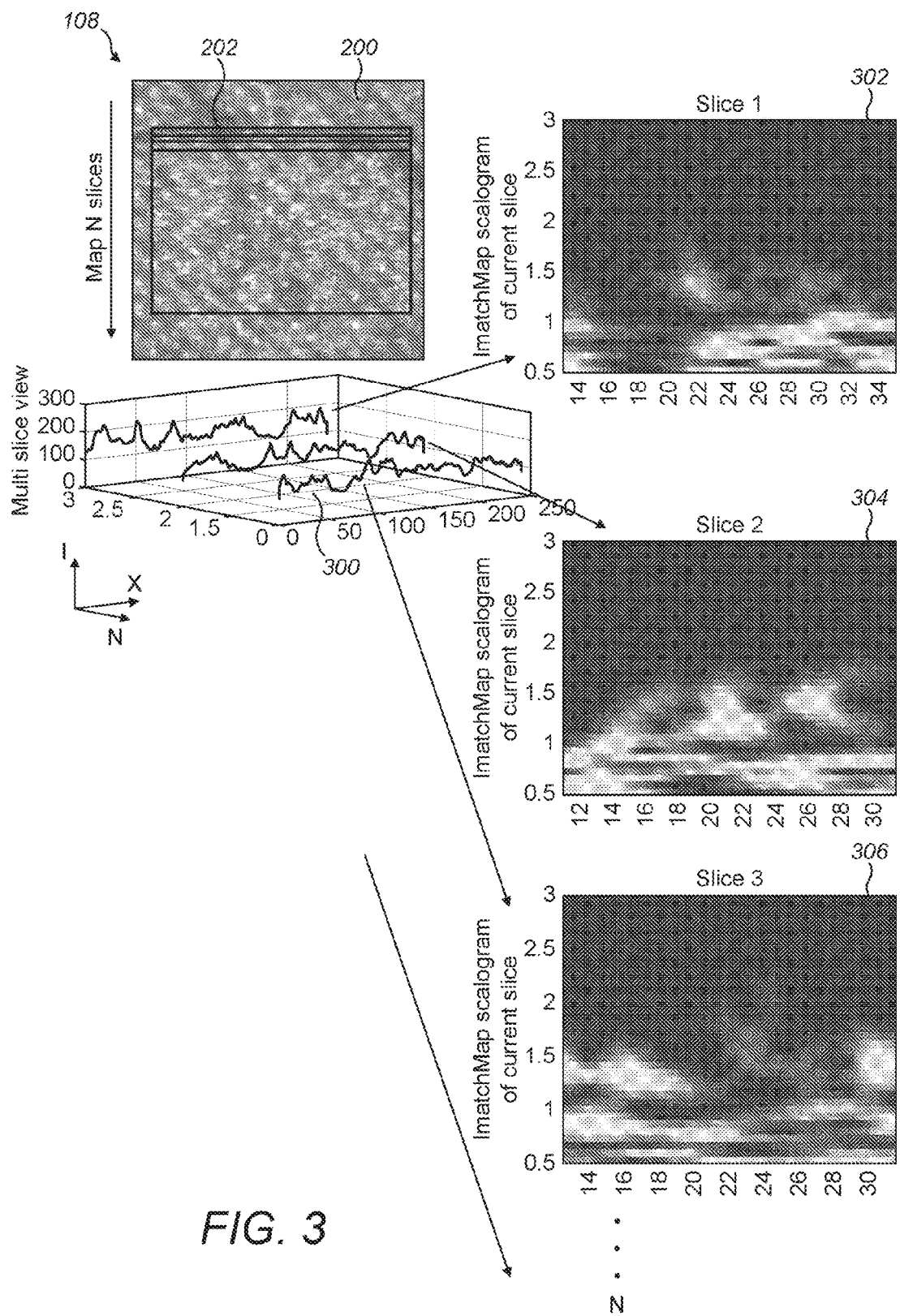
FIG. 3 illustrates aspects of the step of computing a wavelet scalogram of a slice map as illustrated in FIG. 1.

FIG. 3 illustrates aspects of step 108 illustrated in FIG. 1, that of the computation of the wavelet scalogram of the slice map. Plot 300 is a representation of the mapping of the slices illustrated at the top of the region 202 of image 200. The slices (each showing intensity against x position) are shown plotted on an N axis, where N is the integer count number of the slice. Exemplary wavelet scalograms 302, 304 and 306 are shown for first, second and third slices illustrated in representative plot 300. Similar plots are made for each of the N slices present.

In these plots, the x-axis is pixel position (or location along the line of the mapping, commonly given the symbol b); the y-axis is scale (or frequency, commonly given the symbol a). The z-axis is a colour scale where different colours indicate the values of the wavelet transform coefficients (commonly given by notation: T(a,b)), and indicated on a scale running from blue (low values) to red (high values) colour mapping. T(a,b) is given by equation (1) above.

Figure 4:
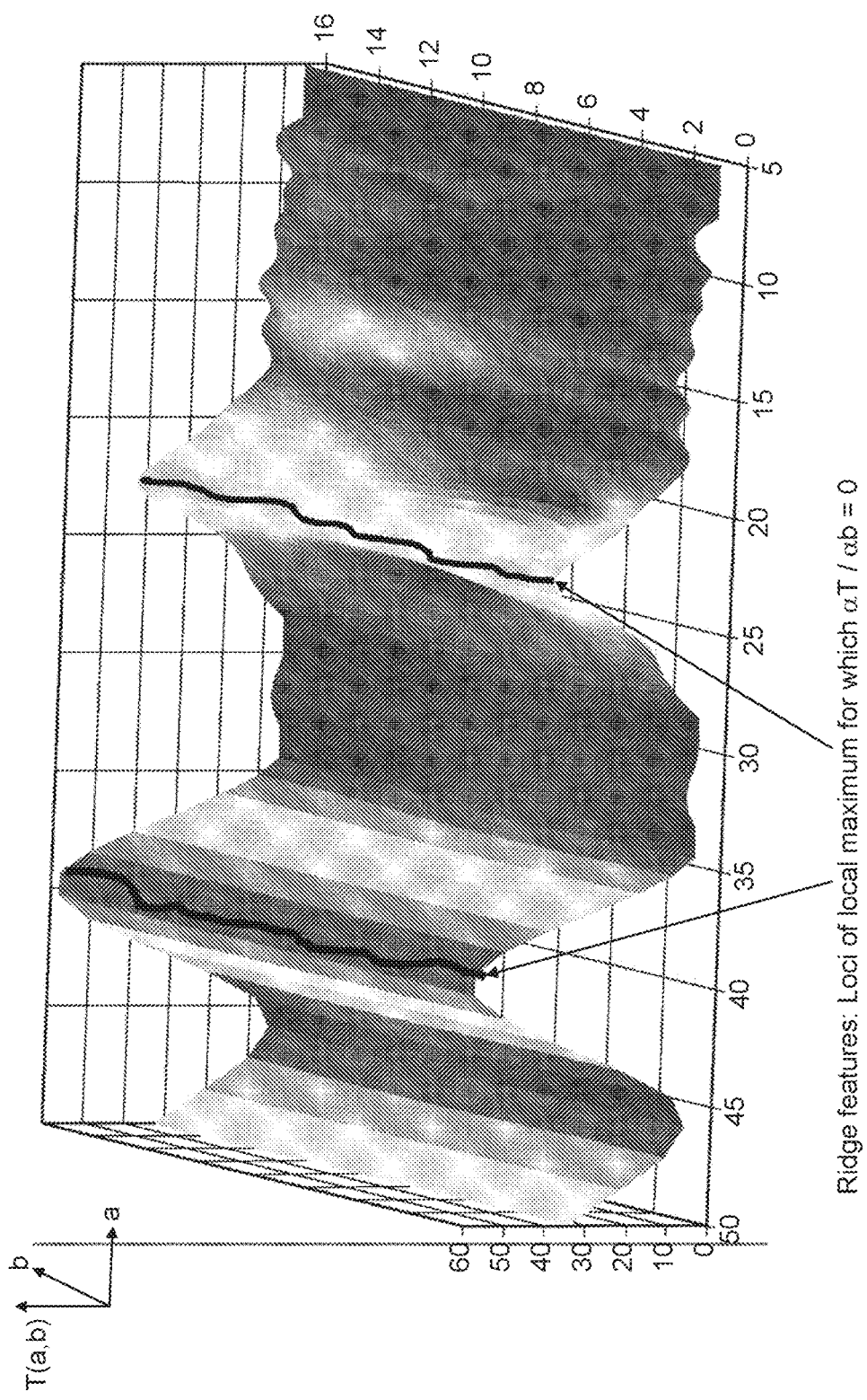
FIG. 4 shows example scalogram ridges, for illustration purposes.

FIG. 4 illustrates the ridges of the scalogram surfaces. In this diagram two ridges are plotted as black lines, representing the local maxima, at which points $\delta T/\delta b=0$.

Figure 5:
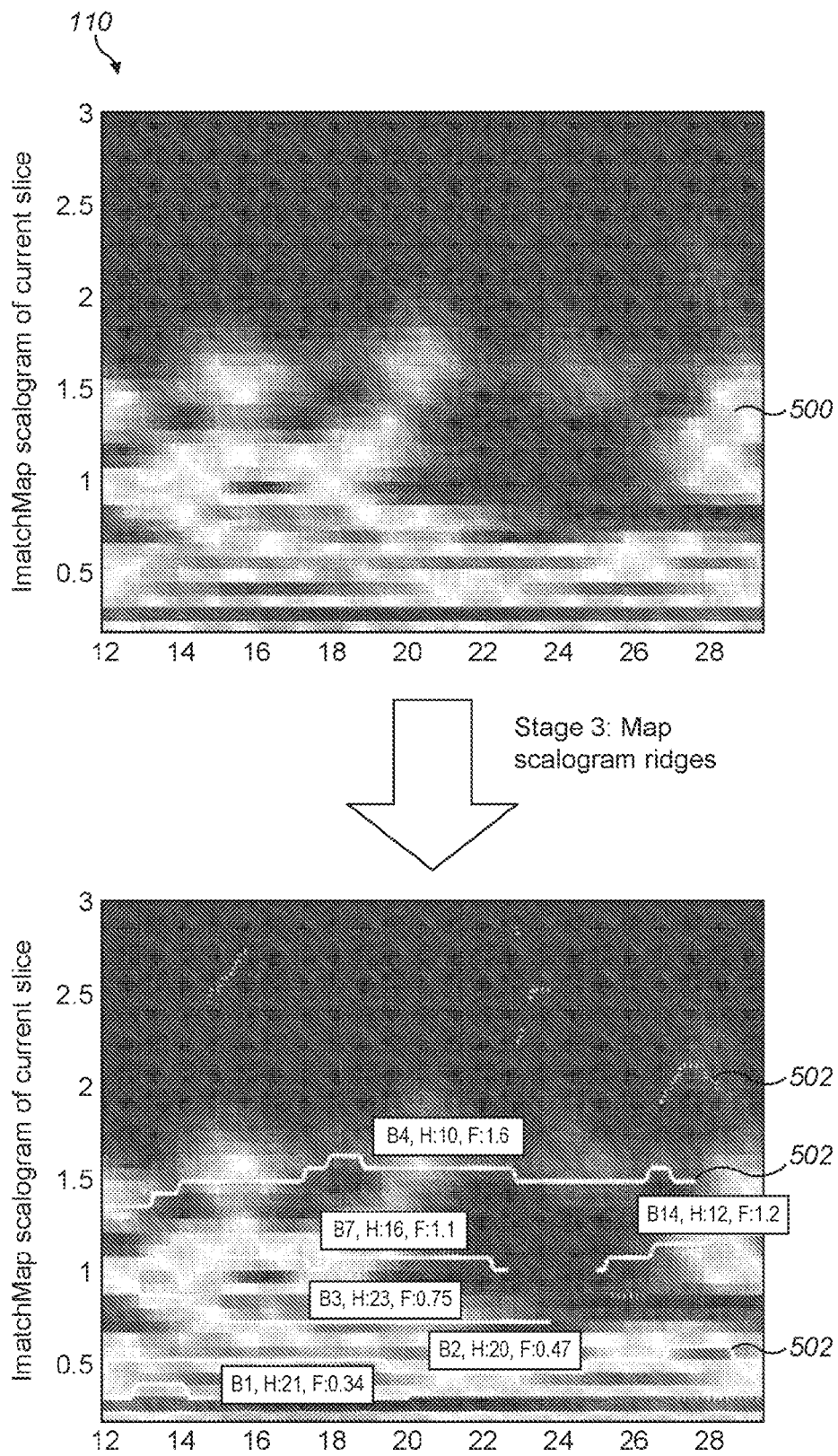
FIG. 5 illustrates aspects of the step of mapping ridge features on a scalogram surface as illustrated in FIG. 1.

FIG. 5 illustrates aspects of step 110 of the algorithm shown in FIG. 1, that of mapping ridge features on the scalogram surfaces. An example scalogram 500 is shown, which is one from the N scalograms illustrated in FIG. 3. In this step, the ridges (illustrated at 502 for example) of the scalogram are mapped and identified, as shown in the bottom half of the figure.

Figure 6:
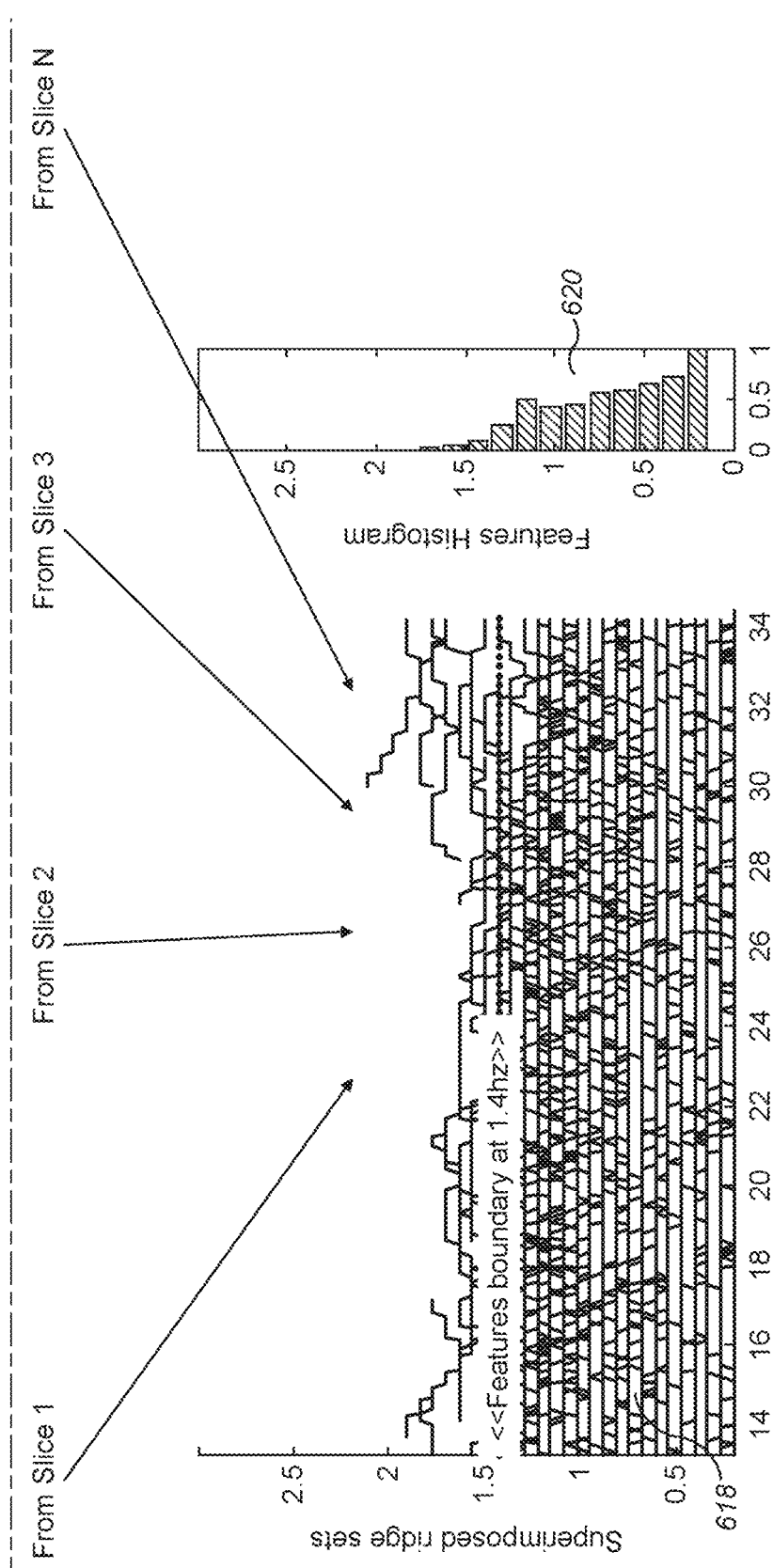
FIG. 6 illustrates aspects of the steps of superimposing ridge features for each slice into a ridge composite mapping, generating a features position histogram and thresholding the histogram, to determine a frequency of upper components as illustrated in FIG. 1.
Figure 7B:
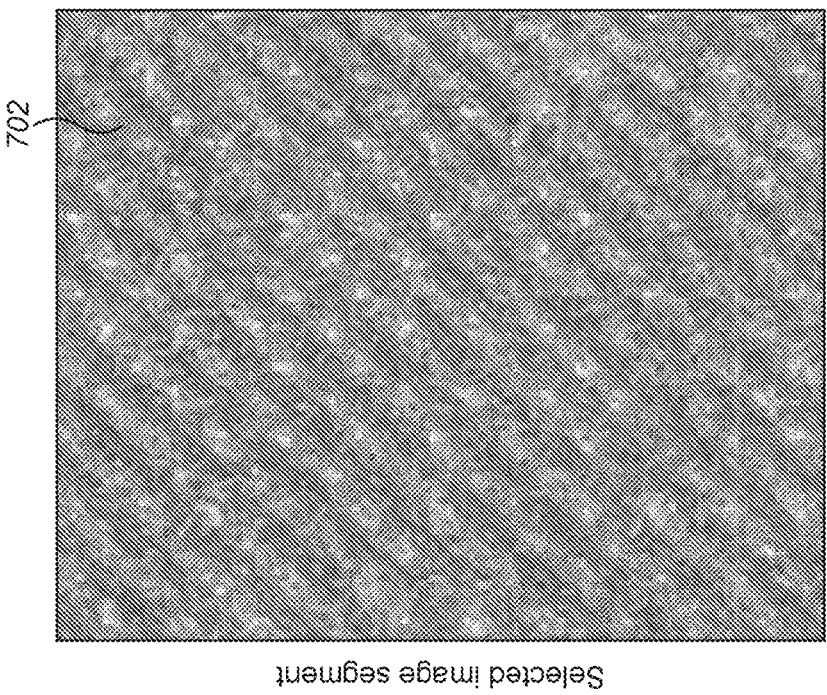
FIG. 7 illustrates aspects of the step of outputting a feature count over an image's selected region as illustrated in FIG. 1.
Figure 7A:
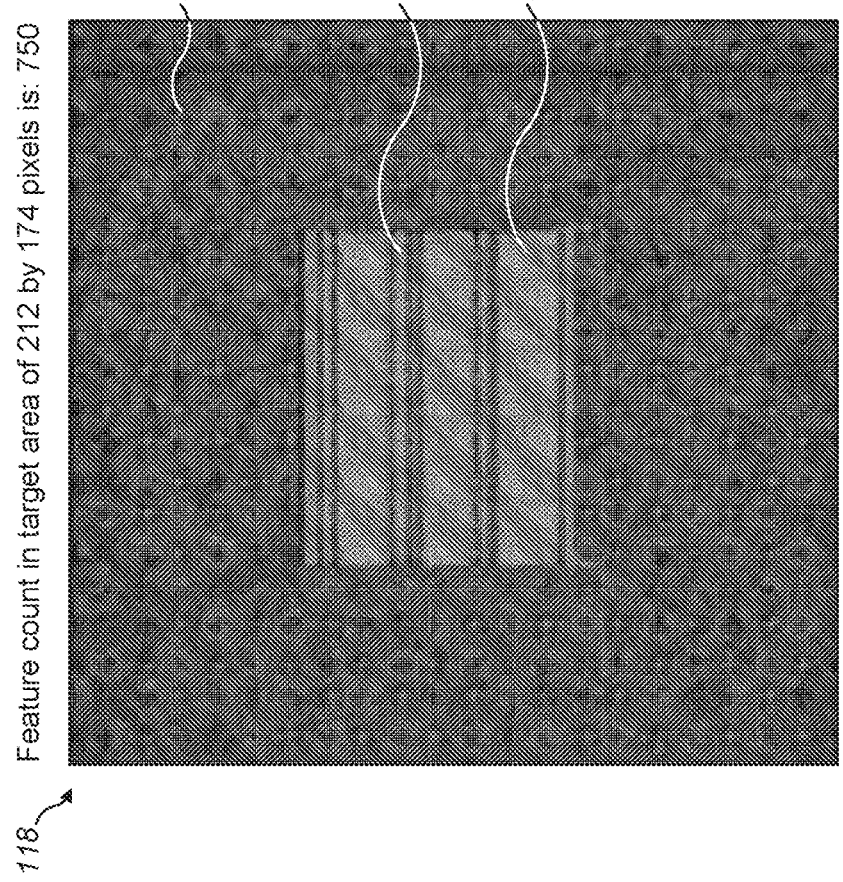
Figure 7C:
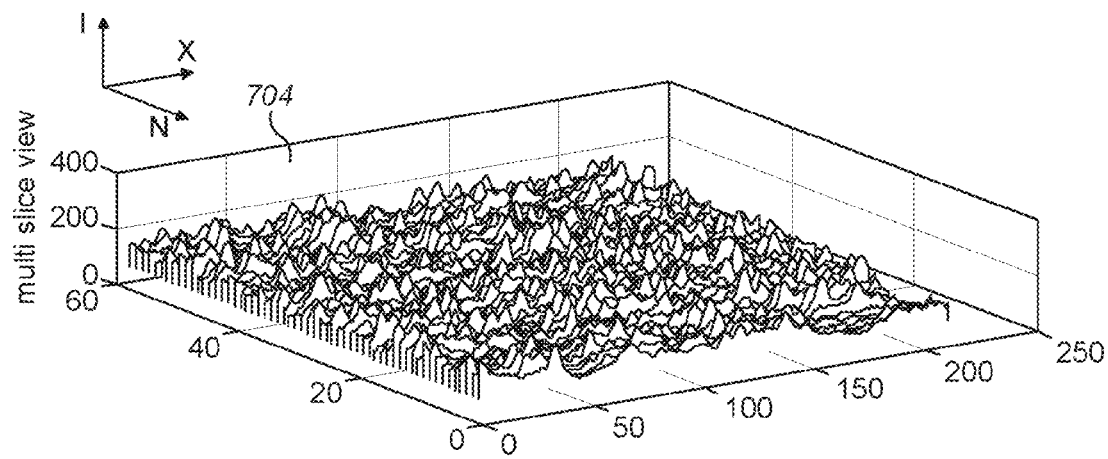
Figure 7D:
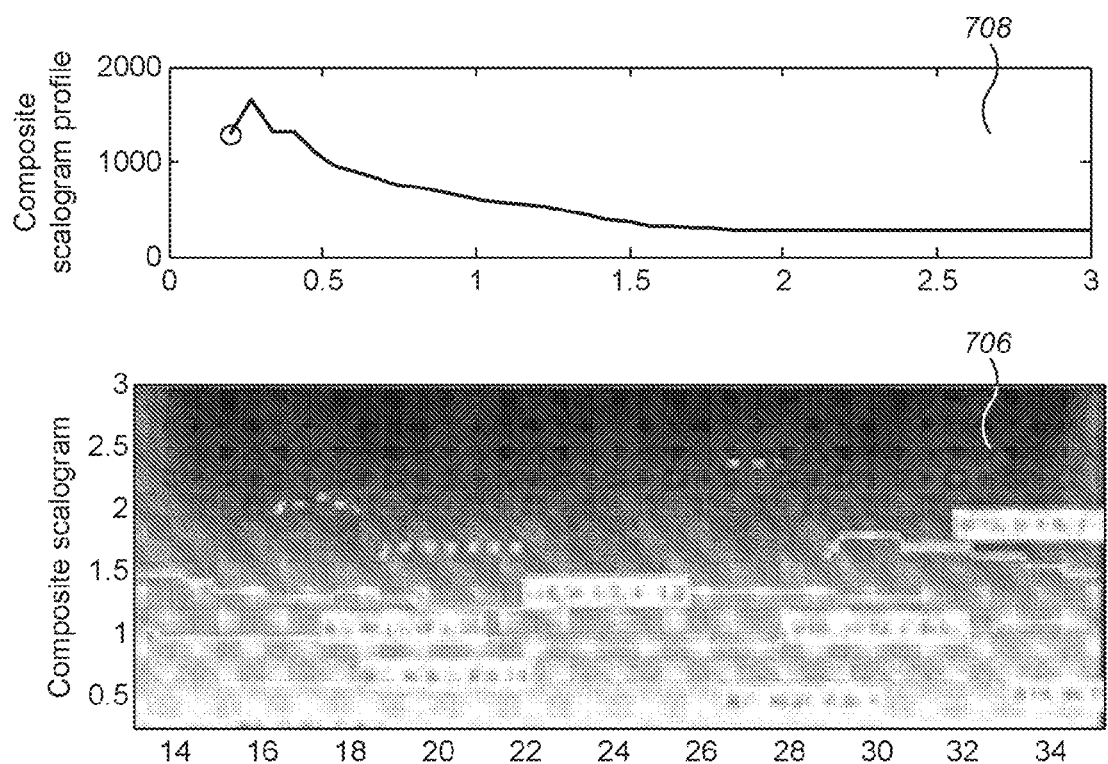
Figure 7E:
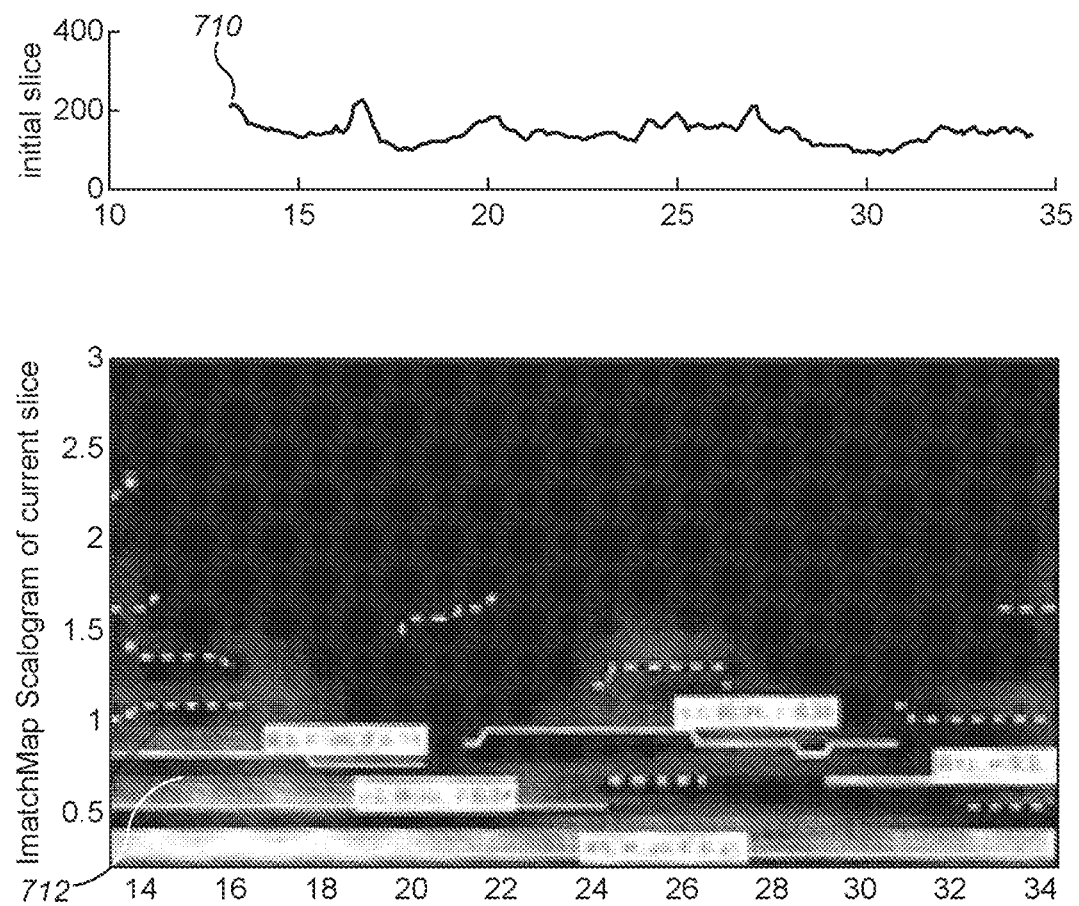
Figure 7F:
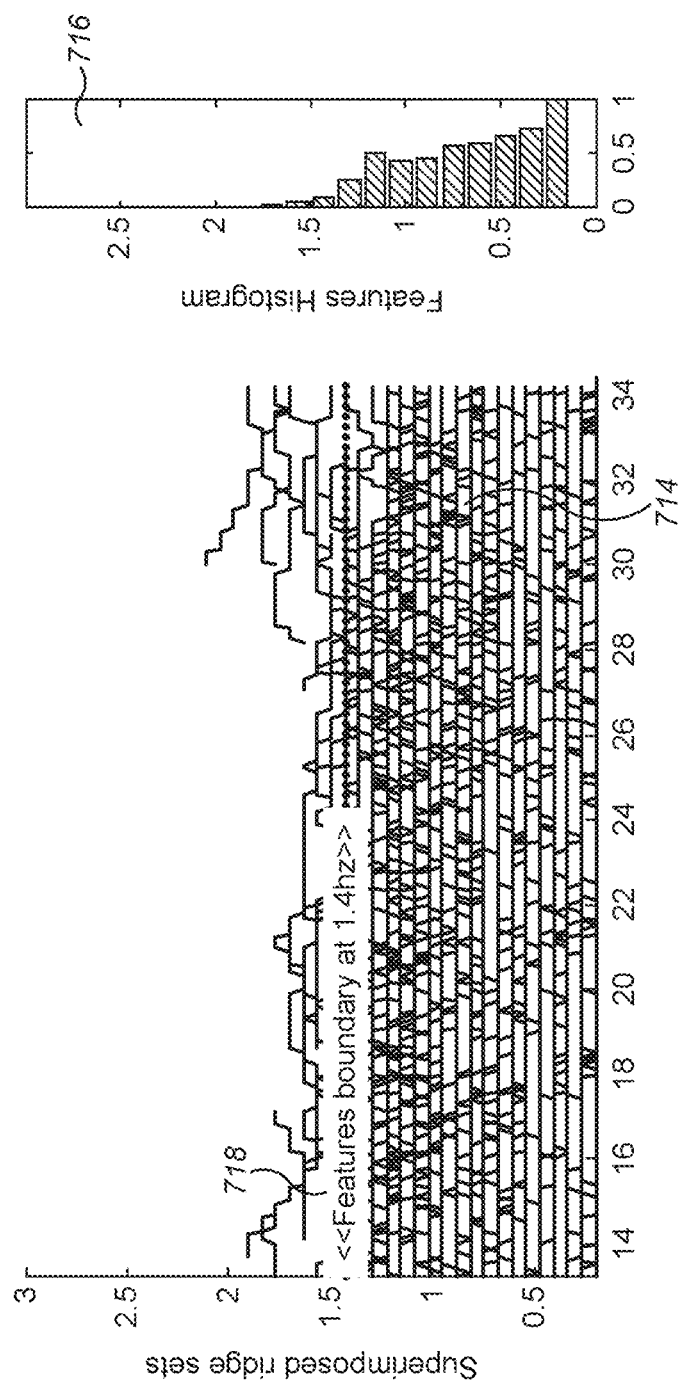

FIG. 6 illustrates aspects of steps 112, 114, 116 illustrated in FIG. 1, those of superimposition of ridge features for each slice into a ridge composite mapping, generation of a featured position histogram from the composite mapping and thresholding from the histogram to determine frequency of upper components. FIG. 6 illustrates wavelet scalograms 600, 602, 604 with mapped wavelet ridges (represented by 606, 608, 610 for example). The ridges can be tagged and classified according to a band index (a ridge ID), and their mean positions in time and frequency.

The ridges are then extracted from the scalograms 600, 602, 604 forming ridge data 612, 614, 616 for each slice. The ridge data are then superimposed (it will be appreciated that the ridge data can be superimposed directly from the scalograms if preferred, there does not have to be a separate extraction step before the superimposition. In either case, the superimposition is performed with the ridge data only, rather than the entire scalogram data). A representation of the superimposed ridges is shown by plot 618 which plots the frequency of the features on ay axis against spatial position in an x axis. It can be seen from the diagram 618 that there is a features boundary at approximately 1.4 on the spatial frequency scale (vertical axis). The superimposed ridges can also be plotted as a histogram 620 which can be thresholded to determine the spatial frequency of the upper components. The frequency of occurrence of the uppermost ridges cluster is used to estimate the spatial density of coherent features that are resolvable just below a base noise level.

These features will correspond to the features for which the wavelet characteristics have been tuned. In one example, the wavelet characteristics can be tuned for the correlation of rod and cone textural features. The characteristic frequency, $f_c$, of the wavelet is tuned to give the maximum resonance (i.e. matched in shape) and the scale range, a, is set so that the size of the features (or size range) is correctly matched.

FIG. 7 illustrates further aspects of the method shown in FIG. 1, the outputting of a feature count over the image selected region. FIG. 7A shows the image 200 with selected region 202. In this instance, all available slices 700 from the region 202 have now been processed. FIG. 7B shows a selected image segment 702. FIG. 7C illustrates a multi slice view, showing the intensity versus spatial position for each of the N slices. FIG. 7D illustrates the composite scalogram 706 and scalogram profile 708. FIG. 7E illustrates a specific slice 710 and its scalogram 712. FIG. 7F illustrates the superimposed ridge sets 714 and the histogram 716 of the superposition. The boundary of feature counts illustrated at 718 is used to deduce the feature density and therefore to provide a count of rod/cone shape occurrences in the image.

Figure 8:
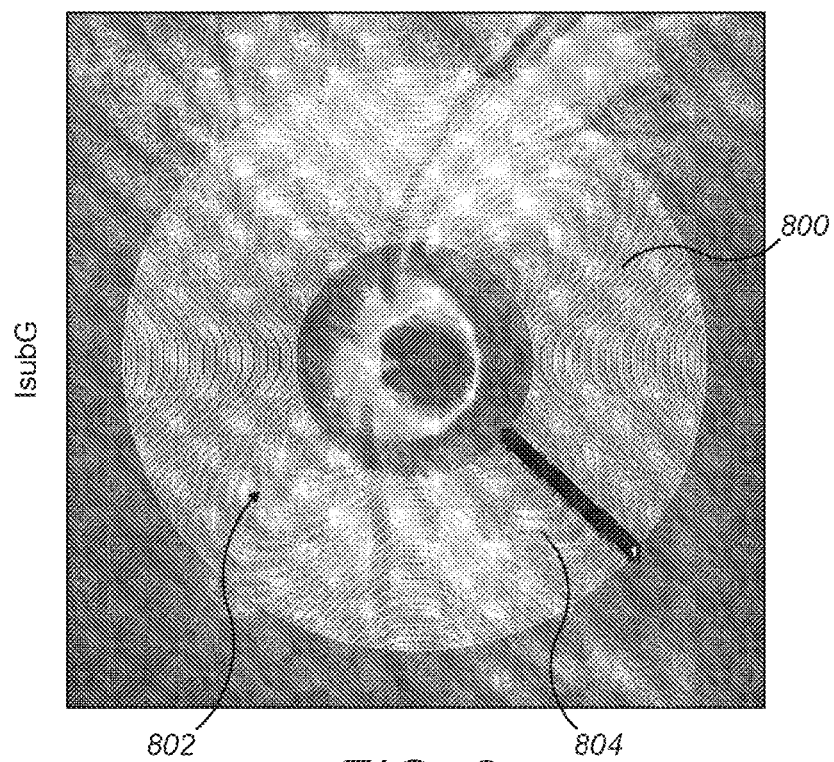
FIG. 8 illustrates an exemplary embodiment for wavelet based surface texture mapping for a retinal image region showing a step where an image is mapped in radial slices.

FIGS. 8 through 13 illustrate an alternative embodiment, wherein an image is mapped in radial slices rather than horizontal slices. As shown in FIG. 8, an image 800 can comprise an annular region of interest 802 which is mapped in a number of different radial slices 804.

Figure 9:
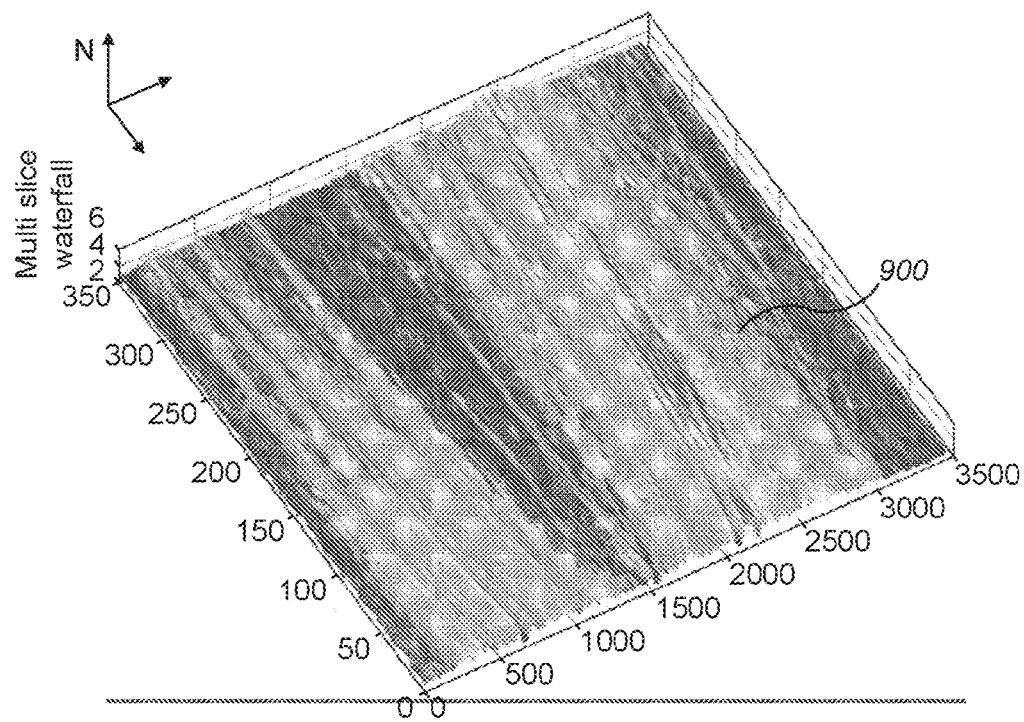
FIG. 9 illustrates the superimposition of slices shown in FIG. 8 in an orthogonal texture image with equal sample intervals.

The slices 804 are superimposed to form an orthogonal texture image 900 as shown in FIG. 9 with equal sample intervals. The diagram represents the concentric circle mappings of FIG. 8 represented as a surface plot, with the y axis representing the radius from the centre of each concentric mapping circle and x axis representing the angular position of mapped points on each of the circles. Oversampling can be used to make sure the 'length' of each map is the same and does not increase with the increasing circumference as the mapping moves away from the centre.

Figure 10:
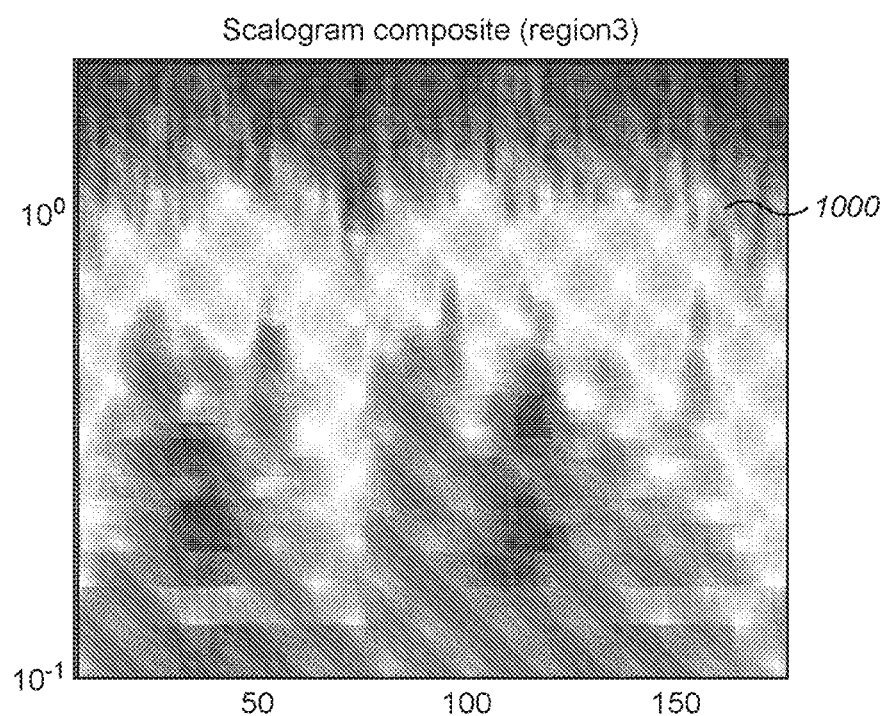
FIG. 10 illustrates the condensing of the information from FIG. 9 into the frequency domain in the form of overlaid scalograms for each slice of the orthogonal texture image.
Figure 11:
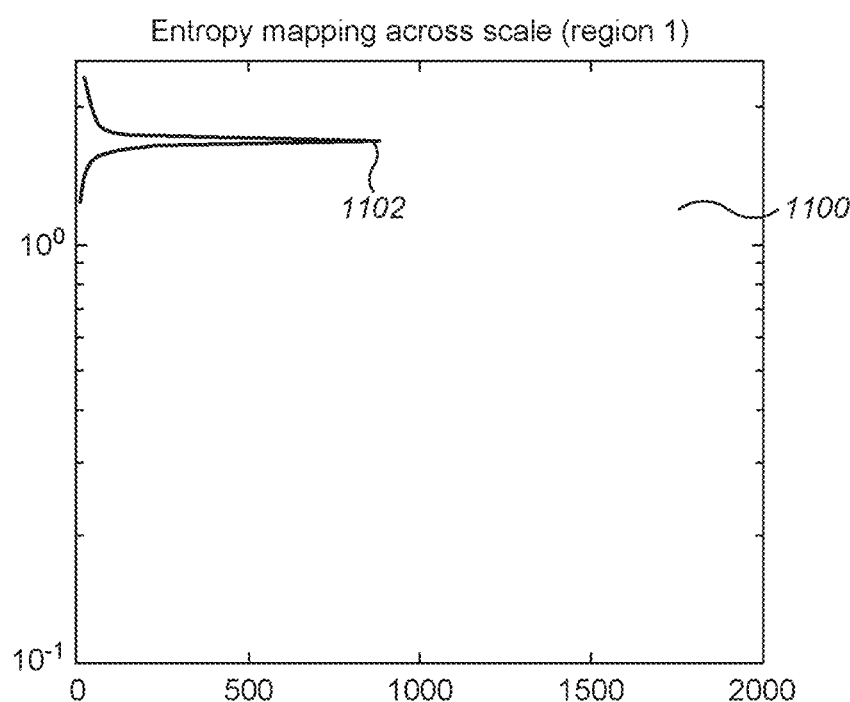
FIG. 11 illustrates a peak in wavelet scale entropy from the diagram of FIG. 10, used to parameterise the retinal texture.

The information is then condensed into the frequency domain in the form of overlaid scalograms for each slice of the orthogonal texture image. A plot of the scalogram composite 1000 is shown in FIG. 10. Entropy is then mapped across the scale, as illustrated in plot 1100 in FIG. 11. The peak 1102 in wavelet scale entropy is then used to parameterise the texture of the image, i.e. the retinal texture in this example.

Figure 12:
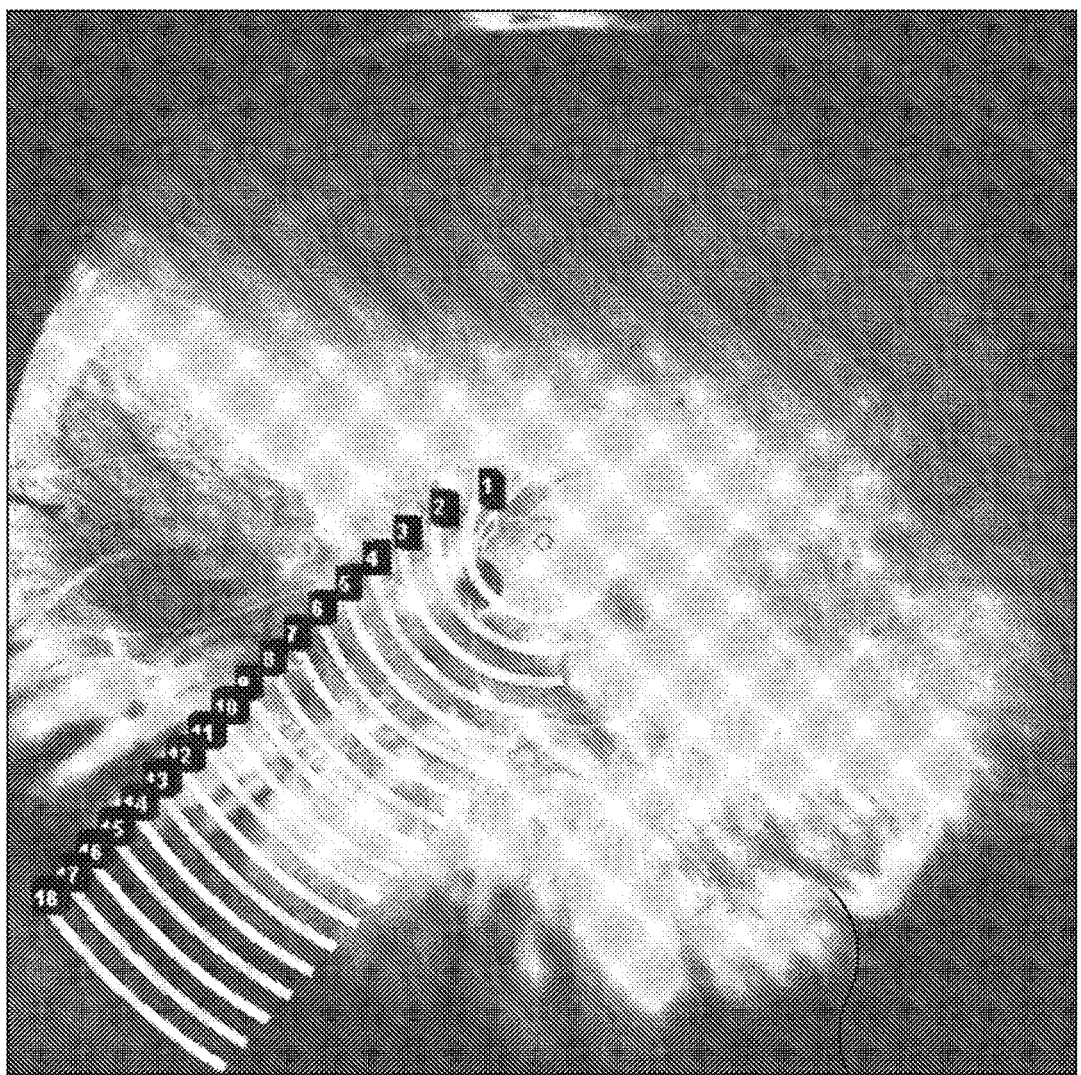
FIG. 12 illustrates a further aspect of wavelet based surface texture mapping for the retinal region showing a step where a radial scan is imaged to map the extent of retinal texture characteristics.
Figure 13:
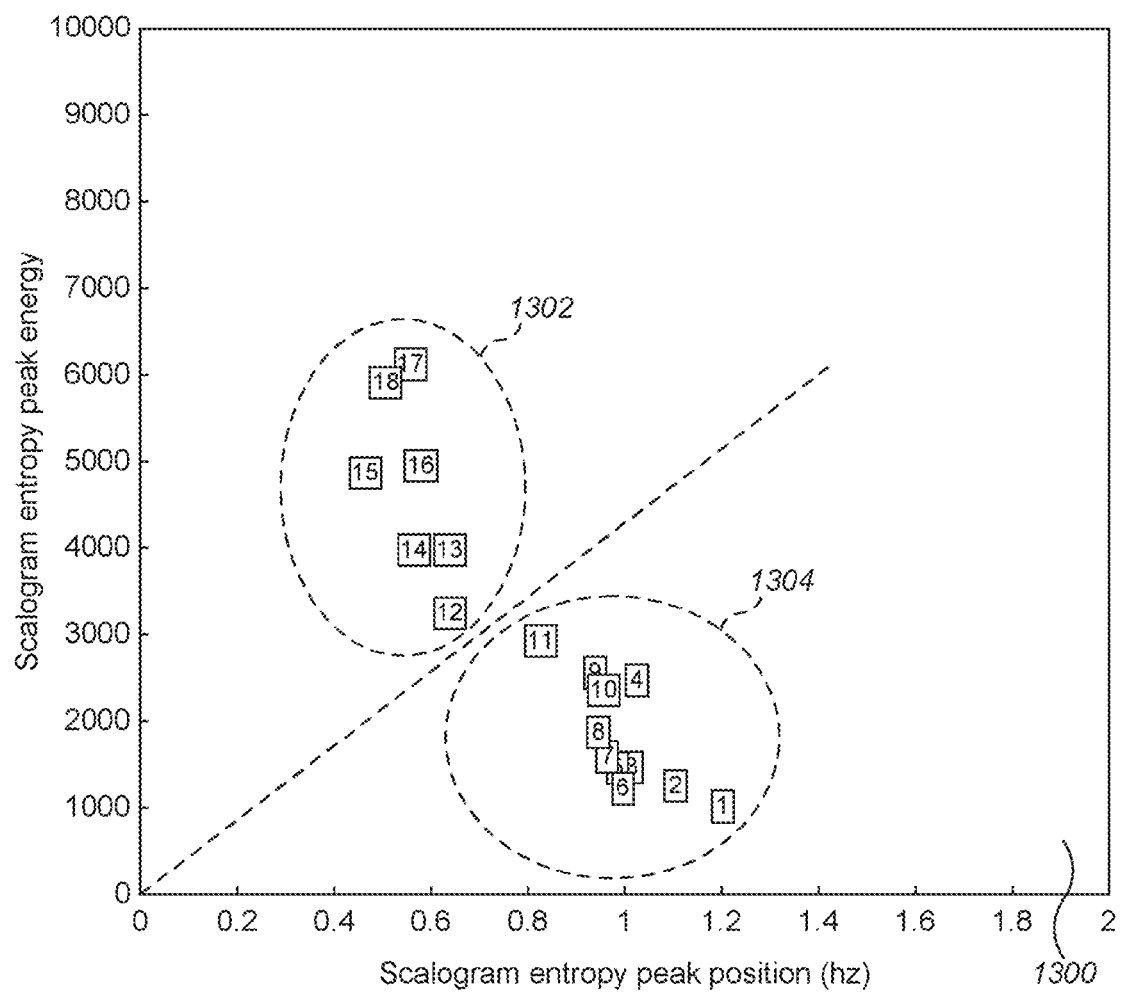
FIG. 13 illustrates the scalogram entropy peak value plotted against scalogram entropy peak position, showing how retinal texture can be partitioned between a set of lid textures and a set of lash textures.

FIG. 12 illustrates a plot 1200 illustrating a further embodiment of a wavelet based surface texture mapping for the retinal region. The regions mapped are shown by the white lines and represent a subset of the radial mappings shown in FIG. 8, defining a limited angular region. From this plot the extent of retinal texture partitioned from lids and lashes textures can be derived, as shown in the plot 1300 of FIG. 13 which illustrates the scalogram entropy peak energy on the y axis versus the scalogram entropy peak position (on a frequency scale and so measured in Hz) on the x axis. If a composite scalogram for each mapped region is taken and the scalogram entropy peak (along scale bands) is found, and then the peak value is plotted against peak position, a set of points is obtained which can discriminate between lashes regions (points 1302 above the dotted line) and retinal texture (points 1304 below the dotted line). This could be used as an automated method of finding the extent of useful retinal texture in an image.

Figure 14:
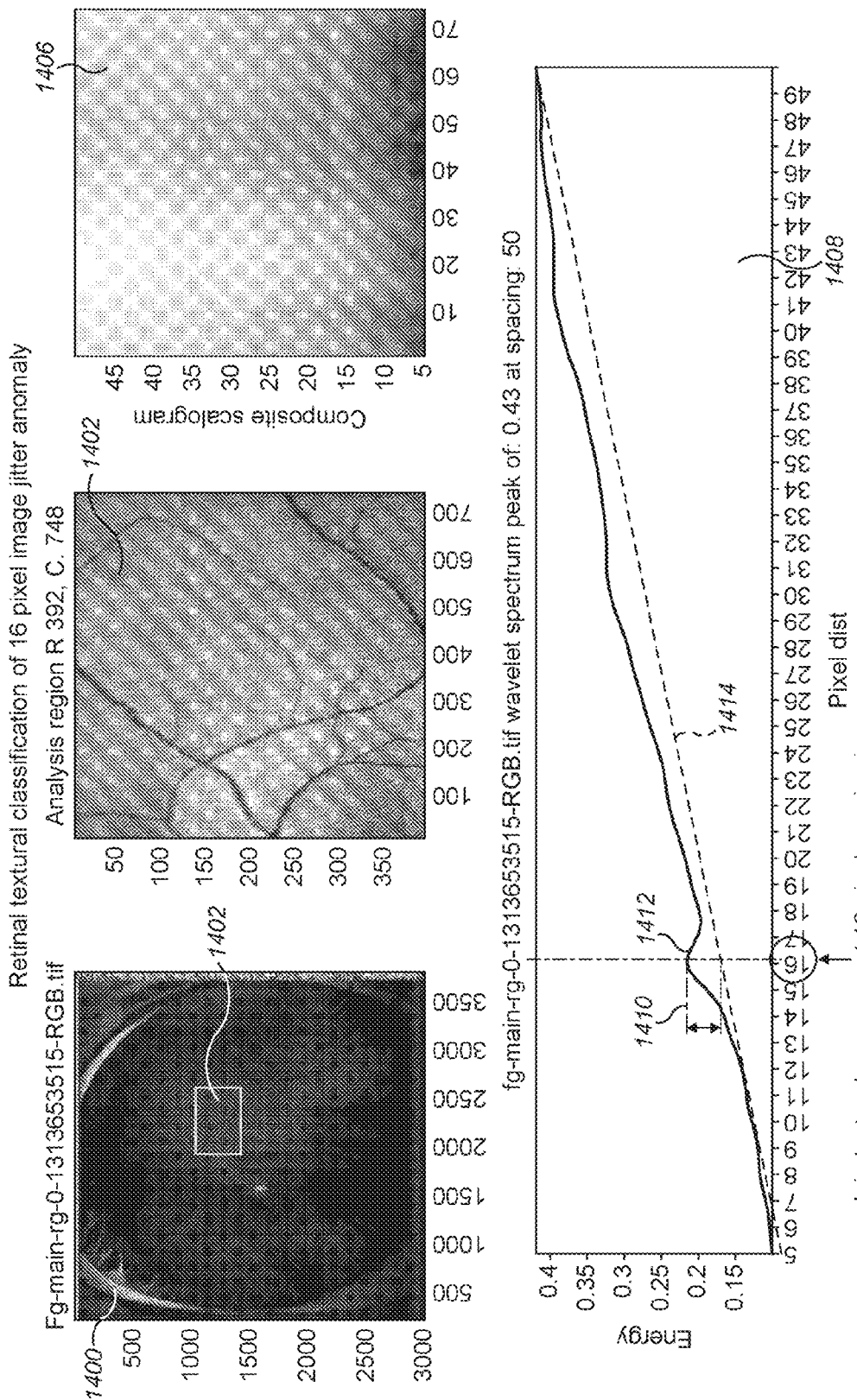
FIG. 14 illustrates an exemplary application of a textural classification method according to an embodiment of the present invention.

FIG. 14 shows an alternative embodiment where the general methods of the algorithm shown in FIG. 1 are used to classify a scanner induced imaging artefact. One of the example instruments in which the present disclosure may be used is a scanning laser ophthalmoscope of the type disclosed in EP 0730428, the contents of which are hereby incorporated by reference. Another example instrument in which the present disclosure may be used is a scanning laser ophthalmoscope of the type disclosed in type is WO 2008/009877, the contents of which are also hereby incorporated by reference. In one example implementation of this type of arrangement, an image scan is carried out by a linear scanner having sixteen individual mirrors (facets) in a polygon arrangement. A reflection along each of these mirrors represents one vertical scan line in the image. A vertical block of sixteen lines represents a single turn of the polygon mirror. If a reflection timing error occurs due to the fact that the inter-mirror angles are not sufficiently accurate, then the vertical position of the line associated with that facet will be displaced in a vertical direction (relative to lines on either side). Timing anomalies from more than one mirror can also occur. This will result in a pattern of timing anomalies in the image (i.e. a displacement pattern of vertical positioning errors) that repeats every sixteen lines across the image. The phenomena is often referred to as 'scanning jitter' (a sixteen-pixel jitter in this particular case). The method of the present disclosure can be used to measure the occurrence of and the intensity of these classes of anomalies.

FIG. 14 shows how these effects can be identified, so that they can be subsequently measured. The diagram shows an image 1400, a selected region 1402 and a composite scalogram 1406 of that region. Plot 1408 then illustrates the energy, summed along each scale band (i.e. summed along rows in the scalogram plot 1406) plotted on they axis versus pixel position on the x axis. The measurement 1410 of the peak 1412 with respect to the linear gradient 1414 gives the pixel jitter metric. The linear ramp could be subtracted from the scalogram summed energy signal give a result that looks more like a conventional spectrum plot. The peak in textural response at the pixel spacing of sixteen in this example is indicative of the degree of sixteen-pixel jitter or timing anomalies information contained within an image.

The various features and methods discussed herein enable automated characterisation of "textural" image features. In general, the algorithm will condense spatial information to provide a compact quantitative description of textural information. The algorithm may have specific application in for example lids and lashes classification and the counting of features in a common class. An example of this could be quantifying (sixteen) pixel jitter in images and the "counting" of rods and cone features in a retinal image. In this latter example the measurement could be relevant as an early indicator to conditions such as Alzheimer's dementia.

The measurement of pixel distortion components or scanner artefacts in a retinal image could also be used for example as a fail/pass criterion in polygon manufacture, where the polygon is of the type disclosed in the European Patent mentioned above.

The use of ridge and scalogram supposition ameliorates noise performance of the measurements made.

Various improvements and modifications may be made to the above without departing from the scope of the disclosure.

For example, "rods and cones" are generally mentioned together in the present disclosure, and are generally of similar size so can be detected as taught above. However it may be possible to further "fine tune" the methods and apparatus of the disclosure to treat rods and cones independently, as the sizing of rods and cones may in some cases be different from each other.

Furthermore, the use of the continuous wavelet transform will in general be preferred, and is described above. However it is possible to use non-continuous wavelet transforms. The above and other variations can be made by the skilled person without departing from the spirit and scope of the invention as defined in the appended claims.

The invention claimed is:

1. A method of image processing, the method comprising:
   (i) selecting, via a processor, a one dimensional slice from an image represented by image data from an image sensor;
   (ii) computing, via the processor, a wavelet scalogram of the slice;
   (iii) identifying, via the processor, ridge features within the wavelet scalogram;
   repeating steps (i), (ii) and (iii) for one or more further slices;
   superimposing, via the processor, the identified ridge features from the slices; and
   deriving, via the processor, textural information from said superimposed identified ridge features.

2. The method of claim 1, wherein said step of deriving textural information from said superimposed identified ridge features comprises thresholding or deriving statistics from a histogram representation of a 2D frequency and scale space spanning the identified ridge features.

3. The method of claim 1, wherein said step of identifying an image along a one dimensional slice comprises selecting a row or column of image data from the image.

4. The method of claim 3, wherein said selected row or column or said path is chosen to have a directionality which corresponds to a directionality of a characteristic of the image which is expected or is being searched for.

5. The method of claim 4, wherein said characteristic of the image is a feature associated with a known pathology or medical condition.

6. The method of claim 1, wherein said step of identifying an image along a one dimensional slice comprises mapping a path along a set of image data pixels to a straight line representation.

7. The method of claim 6, wherein said path along a set of image data pixels comprises a straight line which is angled away from the horizontal or vertical axes defined by the rows and columns of the image data pixels.

8. The method of claim 6, wherein said path along a set of image data pixels comprises a circular path, or part thereof.

9. The method of claim 1, wherein said derived textural information is used to classify regions of a retinal image as comprising either retinal texture, or texture which comprises lid or lashes.

10. The method of claim 9, wherein the regions comprising lid or lash textures are excluded from at least one of a subsequent further image analysis and examination procedure.

11. The method of claim 1, wherein said derived textural information is used to identify scanner-specific image anomalies.

12. The method of claim 1, wherein the step of computing a wavelet scalogram of the slice comprises application of a continuous wavelet transform.

13. The method of claim 12, wherein the step of computing a wavelet scalogram comprises selecting a characteristic frequency of the applied wavelet transform to match a chosen shape.

14. The method of claim 1, wherein the step of computing a wavelet scalogram comprises selecting a scale of an applied wavelet transform to match a chosen feature size.

15. The method of claim 14, wherein a characteristic frequency and a scale are chosen to match the size and shape of at least one of rods and cones in a retina.

16. An image processing apparatus comprising:
   means for receiving image data from an image sensor; and
   a processor arranged to:
      (i) select a one dimensional slice from an image;
      (ii) compute a wavelet scalogram of the slice;
      (iii) identify ridge features within the wavelet scalogram;
      repeat steps (i), (ii) and (iii) for one or more further slices;
      superimpose the identified ridge features from the slices; and
      derive textural information from said superimposed mapped ridge features.

17. The apparatus of claim 16, being arranged to perform a method of image processing, the method comprising:
   (i) selecting a one dimensional slice from an image;
   (ii) computing a wavelet scalogram of the slice;
   (iii) identifying ridge features within the wavelet scalogram;
   repeating steps (i), (ii) and (iii) for one or more further slices;
   superimposing the identified ridge features from the slices; and
   deriving textural information from said superimposed identified ridge features.

18. The apparatus of claim 16 in the form of a laser scanning ophthalmoscope.

19. A computer program product embodied on a non-transitory computer-readable medium encoded with instructions that when run on a computer, cause the computer to receive image data and perform a method of image processing comprising:
   (i) selecting a one dimensional slice from an image;
   (ii) computing a wavelet scalogram of the slice;
   (iii) identifying ridge features within the wavelet scalogram;
   repeating steps (i), (ii) and (iii) for one or more further slices;
   superimposing the identified ridge features from the slices; and
   deriving textural information from said superimposed identified ridge features.

* * * * *